United States Patent [19]
Nakade et al.

[11] Patent Number: 5,592,849
[45] Date of Patent: Jan. 14, 1997

[54] YARN UNEVENNESS INFORMATION ANALYZING APPARATUS

[75] Inventors: Kazuhiko Nakade, Kyoto; Shujiro Suzuki, Mukou; Masakatsu Hasegawa, Uji, all of Japan

[73] Assignee: Murata Kikai Kabushiki Kaisha, Kyoto, Japan

[21] Appl. No.: 559,178

[22] Filed: Nov. 13, 1995

Related U.S. Application Data

[63] Continuation of Ser. No. 132,910, Oct. 7, 1993, abandoned.

[30] Foreign Application Priority Data

Oct. 16, 1992 [JP] Japan ................................. 4-304940

[51] Int. Cl.$^6$ ................ G01N 27/00; G01N 33/36; G06F 19/00
[52] U.S. Cl. ............. 73/160; 57/265; 364/470.14; 364/552; 364/507
[58] Field of Search ..................... 73/160; 57/264, 57/265; 364/507, 552, 470

[56] References Cited

U.S. PATENT DOCUMENTS

| 3,885,232 | 5/1975 | Goto | 73/160 |
|---|---|---|---|
| 4,152,931 | 5/1979 | Mannhart | 73/160 |
| 4,168,604 | 9/1979 | Mannhart | 73/160 |
| 4,430,720 | 2/1984 | Aemmer | 364/552 |
| 4,491,831 | 1/1985 | Sakai et al. | 57/264 |
| 4,774,673 | 9/1988 | Aemmer | 364/552 |
| 5,124,928 | 6/1992 | Aemmer | 364/470 |
| 5,178,008 | 1/1993 | Aemmer | 364/552 |

*Primary Examiner*—Diego F. F. Gutierrez
*Attorney, Agent, or Firm*—Armstrong, Westerman, Hattori, McLeland & Naughton

[57] ABSTRACT

A yarn unevenness information analyzing apparatus which can perform an analysis of periodic yarn unevennesses without being restricted by another analysis of non-periodic yarn unevennesses. Signals from a large number of yarn evenness detectors are inputted to a CPU for yarn unevenness analysis by way of a first switch for changing over the signals in a short period to successively output the signals and a second switch for changing over the signals in a long period to successively output the signals.

6 Claims, 10 Drawing Sheets

| | | |
|---|---|---|
| 3 — | THIN PLACE | SHORTER THAN ABOUT 8cm & THINNER THAN -30% |
| 2 — | THICK PLACE | SHORTER THAN ABOUT 8cm & THICKER THAN +35% |
| 1 — | NEP * | SHORTER THAN ABOUT 4mm & LARGER THAN +140% |

\* FOR NEP, CONVERTED PER 1mm

YARN UNEVENNESS DETECTOR

YARN UNEVENESS INFORMATION ANALYZING APPARATUS

This application is a continuation of application Ser. No. 08/132,910 filed Oct. 7, 1993, now abandoned.

BACKGROUND OF THE INVENTION

1. Field of the Invention

This invention relates to a yarn unevenness information analyzing apparatus for detecting a yarn unevenness in a spinning machine including a large number of spinning units.

2. Prior Art

Figures 9, 10:
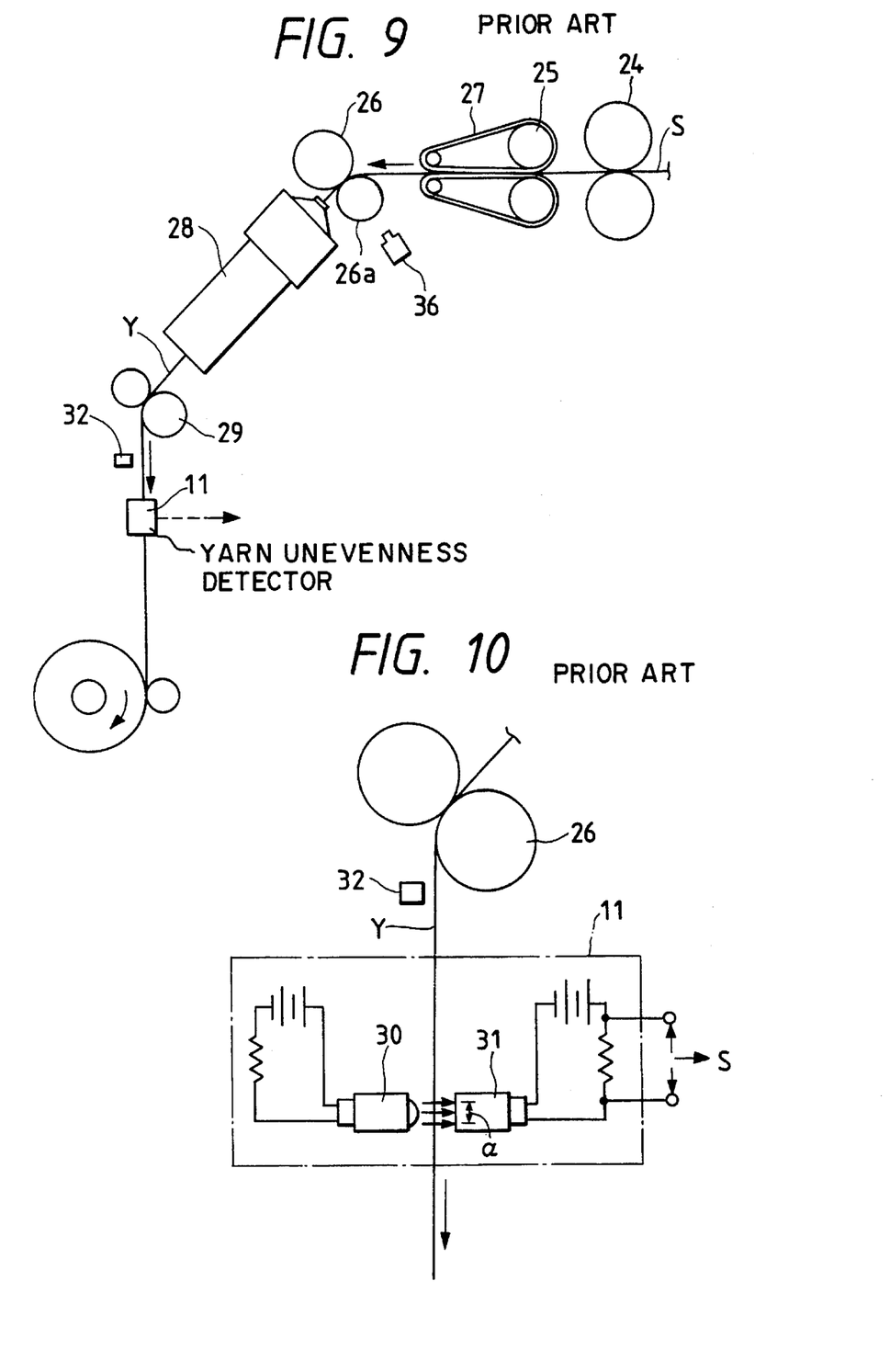
FIG. 9 is a view showing essential part of a spinning unit.
FIG. 10 is a detailed view of a yarn unevenness detector.

One of spinning machines which include a large number of spinning units is a pneumatic spinning machine and is shown, for example, in FIGS. 3 and 4 of the official gazette of Japanese Patent Laid-Open Application No. Heisei 2-221427. The pneumatic spinning machine is described with reference to FIGS. 9 and 10. FIG. 9 is a view showing essential part of each spinning unit. Referring to FIG. 9, reference numeral 24 denotes a back roller, 25 a middle roller, and 26 a front roller, and an apron 27 in the form of an endless rubber belt extends around the middle roller 25. Each of the rollers 24, 25 and 26 includes a top roller at an upper position and a bottom roller at a lower position and performs drafting of a sliver S. Reference numeral 28 denotes an air jet nozzle, which twists the sliver S coming out from the front roller 26 to produce a spinning yarn Y. Reference numeral 29 denotes a delivery roller for drawing out the yarn from the spinning nozzle 28, and 11 a yarn unevenness detector, that is, a slub catcher, of the photoelectric conversion type for detecting a variation of the thickness of the yarn Y to output a yarn unevenness signal. It is to be noted that a yarn speed is detected by means of a sensor 36 located in the proximity of the lower front roller 26a. The yarn speed is controlled by a master computer not shown for the entire spinning machine.

FIG. 10 is a detailed view of the yarn unevenness detector. Referring to FIG. 10, the yarn unevenness detector or slub catcher 11 is a detector 11 of a high sensitivity and a high responsibility of the type which includes a light emitting diode 30 and a phototransistor 31 and detects an amount of light emitted from the light emitting diode 30 by means of the phototransistor 31 and outputs the amount of light thus detected as an electric displacement between terminals. When a slub is encountered and a very large displacement of the amount of electricity is detected, a cutting apparatus 32 operates in response to the signal to cut the yarn Y at the location. The electric signal from the yarn unevenness detector or slub catcher 11 is utilized as a yarn unevenness analysis signal.

The electric signal from the yarn unevenness detector is conventionally analyzed generally in the following manner. In particular, the electric signal is converted into a digital signal and then processed by Fourier transform or integration processing for a fixed section. The signal after such Fourier transform is analyzed by spectrum analysis, and it is specified from a frequency of a peak portion of the signal by which one of rollers of the spinning unit a periodic unevenness is caused. The result of the spectrum analysis is used principally as maintenance information of the spinning machine so that maintenance of the spinning machine is performed. Meanwhile, the signal processed by integration processing represents a total amount of non-periodic yarn unevennesses and is used as quality information of the yarn.

By the way, while the analysis time for periodic yarn unevennesses described above is as short as one minute or so since the frequency of occurrence of the periodic yarn unevennesses is equal to the period of rotation of a roller or the like, the analysis time for non-periodic yarn unevennesses is as long as 4 to 10 minutes or so since the frequency of occurrence of such non-periodic yarn unevennesses is low. In the spinning machine described above, signals from different spinning units are successively changed over by means of a multiplexer or the like to analyze them by means of a single analyzing apparatus. Accordingly, there is a problem in that the interval of analyses of periodic yarn unevennesses for different spinning units, which are required to be performed rapidly in order that results of them may be used for maintenance, is long.

SUMMARY OF THE INVENTION

The present invention has been made in view of such a problem of the prior art as described above, and it is a first object of the present invention to provide a yarn unevenness information analysis apparatus which can make an analysis of periodic yarn unevennesses without being restricted by an analysis of non-periodic yarn unevennesses.

Meanwhile, it is a second object of the present invention to provide a yarn defect detection method by which a defect of a yarn can be specified from a thickness in section and a length of a defective portion of a yarn on the on-line real-time basis.

In order to achieve the first object described above, a yarn unevenness information analyzing apparatus according to the present invention is constructed such that signals from a large number of yarn unevenness detectors are inputted to calculation means for yarn unevenness analysis by way of first changeover means for changing over the signals in a short period to successively output the signals and second changeover means for changing over the signals in a long period to successively output the signals.

The yarn unevenness information analyzing apparatus of the present invention can make an analysis of yarn unevennesses of a short period without being restricted by another analysis of yarn unevennesses of a long period (including non-periodic yarn unevennesses) since signals from a large number of yarn unevenness detectors are inputted to calculation means for yarn unevenness analysis by way of first changeover means for changing over the signals in a short period to successively output the signals and second changeover means for changing over the signals in a long period to successively output the signals.

In order to attain the second object described above, according to a yarn defect detection method of the present invention, a signal from a detector for detecting the thickness of a yarn being fed is sampled for each unit time, and a short and very thick yarn detect is detected from an elapsed time from a signal immediately before the sampled signal becomes higher than a predetermined threshold value to another signal immediately after the sampled signal becomes lower than the predetermined threshold value and an accumulated value of such sampled signals.

Since accumulation is started from a signal immediately before the sample signal becomes higher than a predetermined threshold value and is performed to another signal immediately after the sampled signal becomes lower than the predetermined threshold value and an accumulated value of such sampled signals, a short defect with which the sampling number is small relative to the defect length can be detected accurately.

Meanwhile, in order to achieve the second object described above, according to a yarn defect detection method of the present invention, a signal from a detector for detecting the thickness of a yarn being fed is sampled for each unit time, and a thin and long yarn defect is detected from an elapsed time from a signal which becomes lower than a lower limit value lower than a predetermined threshold value to another signal which becomes higher than an upper limit value higher than the predetermined threshold value.

Further, the yarn defect detection method may be constructed such that a signal from a detector for detecting the thickness of a yarn being fed is sampled for each unit time, and a thick and long yarn defect is detected from an elapsed time from a signal which becomes higher than an upper limit value higher than a predetermined threshold value to another signal which becomes lower than a lower limit value lower than the predetermined threshold value.

Since accumulation is started from a signal which becomes lower than a lower limit value lower than a predetermined threshold value and is performed to another signal which becomes higher than an upper limit value higher than the predetermined threshold value, a thin and long defect can be detected accurately even from a variation of the signal of a value in the proximity of the threshold value.

Meanwhile, since accumulation is started from a signal which becomes higher than an upper limit value higher than a predetermined threshold value and is performed to another signal which becomes lower than a lower limit lower than the predetermined threshold value, a thick and long defect can be detected accurately even from a variation of the signal of a value in the proximity of the threshold value.

DETAILED DESCRIPTION OF PREFERRED EMBODIMENT

Figure 1:
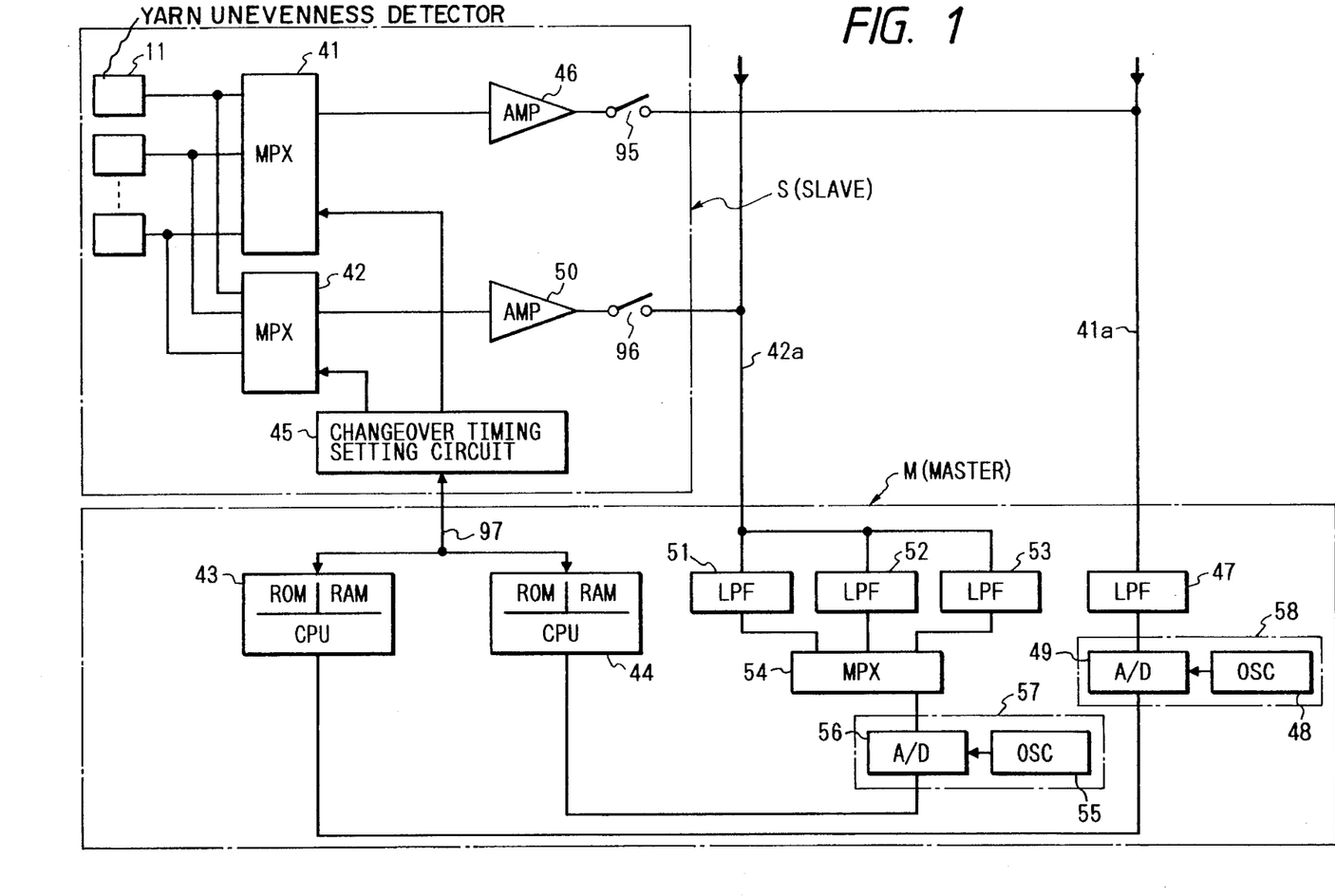
FIG. 1 is a block diagram showing construction of a yarn unevenness information analyzing apparatus in which a yarn defect detection method of the present invention is used.
Figure 2:
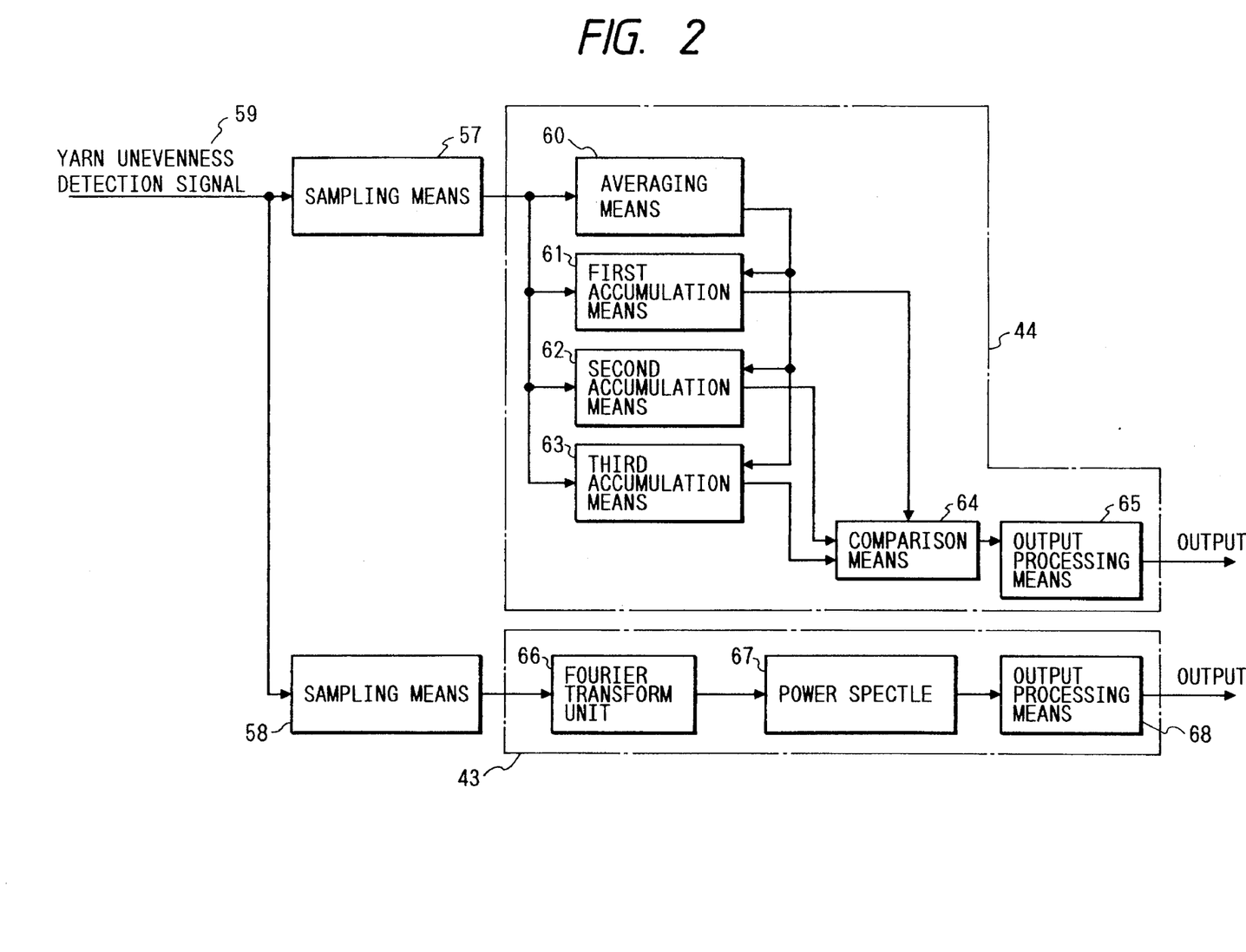
FIG. 2 is a block diagram showing calculation means of the yarn unevenness information analyzing apparatus of FIG. 1.

In the following, an embodiment of the present invention will be described with reference to the drawings. FIG. 1 is a block diagram showing construction of a yarn unevenness information analyzing apparatus in which a yarn defect detection method of the present invention is used, and FIG. 2 is a block diagram showing calculation means of the yarn unevenness information analyzing apparatus of FIG. 1.

Referring to FIG. 1, reference character S denotes a slave provided for each span of a spinning machine, and M an analyzing apparatus master installed commonly to a plurality of such slaves S. The slaves S and the master M are connected to each other by way of analog lines 41a and 42a and a communication line 97. The analog line 41a performs transmission only of an analog signal for analysis of periodic (only short periodic) yarn unevennesses while the analog line 42a performs transmission only of an analog signal for analysis of non-periodic yarn unevennesses (including unevennesses of a long period), and communication is performed by way of the communication line 97. Analyses for the slaves S are performed by successively changing over changeover means 95 and 96. Electric signals from yarn unevenness detectors 11 mounted on spinning units belonging to the slaves S are sent out to first and second multiplexers 41 and 42 serving respectively as first and second switching over means, and extraction timings of the multiplexers 41 and 42 are set by a changeover timing setting circuit 45. The changeover periods of the changeover means 95 and 96 being different from each other. The electric signal extracted from the first multiplexer 41 is inputted by way of an amplifier 46 and a low-pass filter 47 to sampling means 58 constituted from an oscillator 48 and an analog to digital converter 49, and the electric signal is converted into a digital signal by the sampling means 58 and sent out to a first CPU 43. Meanwhile, the electric signal extracted from the second multiplexer 42 passes one of first to third low-pass filters 51 to 53, which are suitably changed over by a multiplexer 54, by way of an amplifier 50 and is inputted to sampling means 57 constituted from an oscillator 55 and an analog to digital converter 56, and the electric signal is converted into a digital signal by the sampling means 57 and sent out to a second CPU 44. It is to be noted that the sampling means 57 and 58 sample input signals thereto by means of the accurate oscillators 48 and 55, which make data sampling times determined in accordance with frequencies required for analyses, so that they are converted into digital signals.

The phrase "for changing over the signals in a short period" used herein, and the phrase "for changing over the signals in a long period" used herein, are explained further as follows. The first (second) changeover means 41 (42) changes over in order the input signals from n numbers of yarn unevenness detectors 11 and outputs a signal to the calculation means. More specifically, the phrase "for changing over the signals in a short (long) period" means that in short period, the input signal from the n numbers of yarn unevenness detector 11 is changed over, for example, in about one minute, and in a long period, it is changed over, for example, in about ten minutes. In another words, n number of yarn unevenness detectors 11 are changed over in order in every predetermined short (long) period and one of the yarn unevenness detector is connected to the calculation means.

Subsequently, referring now to FIG. 2, the digital signal inputted to the first CPU 43 is calculated by a Fourier transform unit 66, and a result of the calculation is composed into a power spectrum by vector composition by vector composition means 67, whereafter it is processed by output processing means 68 so as to be suitable for an analysis and then outputted to the outside. Meanwhile, the digital signal inputted to the second CPU 44 is processed by averaging means 60 so as to calculate an average value of it, and elapsed times and accumulated values regarding a nep (short and very thick yarn defect), a thick place (thick and long yarn defect) and a thin place (thin and long yarn defect) are calculated from the average value and the digital signal by first to third accumulation means 61 to 63, respectively. Results of the accumulations are compared with preset values by comparison means 64 to determine presence or absence of a defect and then processed by output processing means 65 so as to be suitable for analyses, whereafter they are outputted to the outside.

Subsequently, concrete examples of programs incorporated in the first to third accumulation means 61 to 63 of FIG. 2 will be described with reference to FIGS. 3, 4 and 5.

Figure 3:
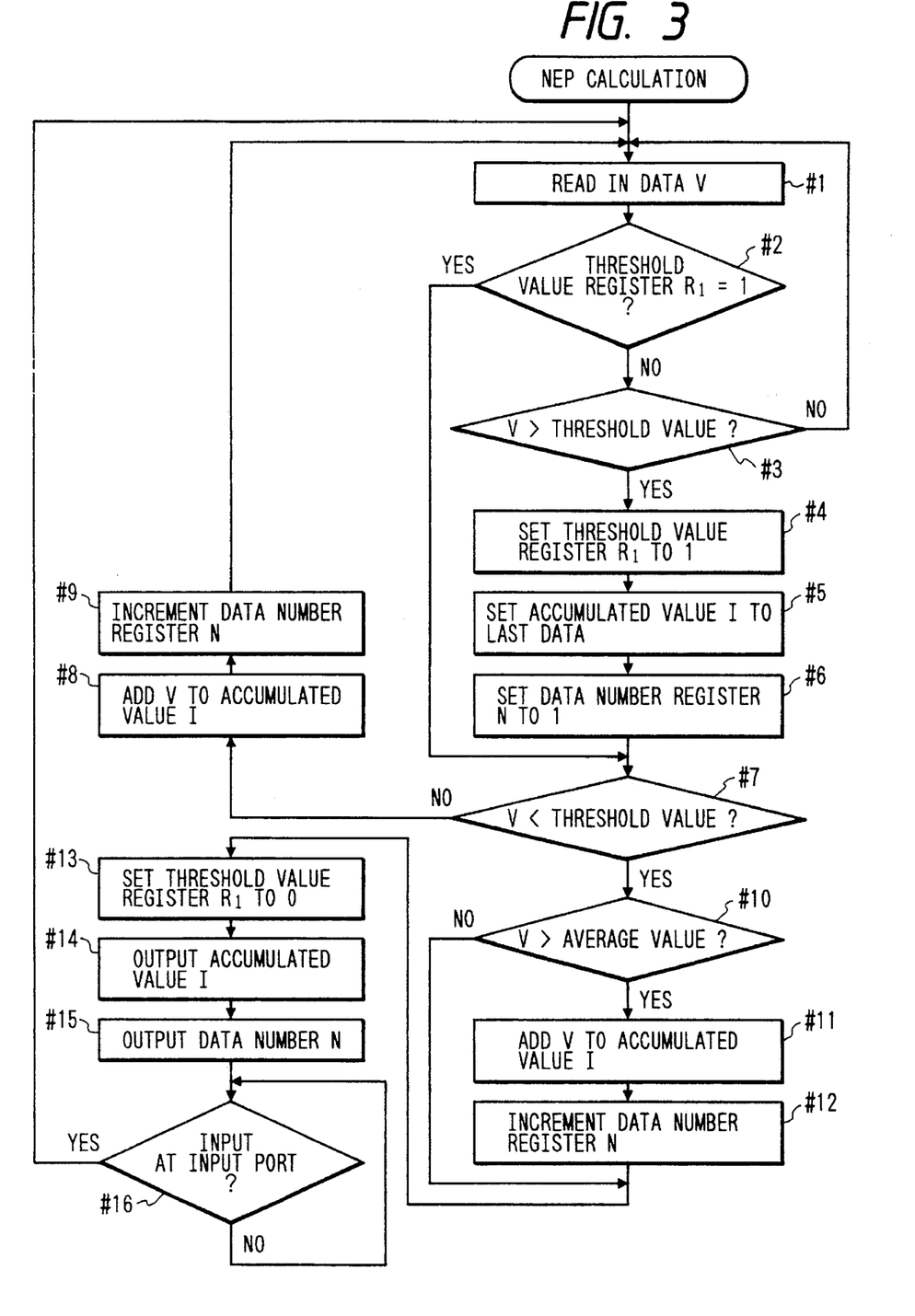
FIG. 3 is a flow chart of a nep calculation.

FIG. 3 is a flow chart for a nep calculation incorporated in the first accumulation means 61. Referring to FIG. 3, when an input is received (step #16), data V (digital signal) is read in (step #1), and since a threshold value register $R_1$ is set to 0 in advance, the data V is compared with the threshold value to determine whether or not it is higher than the threshold value (steps #2 and #3). When the data V exceeds the threshold value, the threshold value register $R_1$ is set to 1 (step #4), and contents of an accumulated value I are set to a data value obtained immediately before the data V becomes higher than the threshold value (step #5), whereafter a data number register N is incremented by one (step #6). Subsequently, the data V is compared with the threshold value to determine whether or not it is lower than the threshold value (step #7), and when the data V is higher than the threshold value, the data V is added to the contents of the accumulated value I (step #8) and the data number register N is incremented by one (step #9), whereafter the control sequence returns to step #1, at which next data V is read in. Then, since the threshold value register $R_1$ has been set to 1, the control sequence advances to step #7, at which the data V is compared with the threshold value to determine whether the data V is lower than the threshold value (steps #2 and #7). Thereafter, the steps described above are repeated until after the data V becomes lower than the threshold value. After the data V becomes lower than the threshold value, it is compared with the average value (step #10), and then if it is higher than the average value, it is added to the accumulated value I (step #11) and the data number is counted (step #12). However, when the data V is lower than the average value, it is not added to the accumulated value I and is not counted into the data number either. This is because, when the data V is lower than the average value, the calculation substantially becomes subtraction and this is contrary to the object to add also such data that are lower than the threshold value to compensate for shortage of the number of data. Further, the data number may be counted. Subsequently, the threshold value register $R_1$ is reset (step #13), and then the accumulated value I and the data number N are outputted (steps #14 and #15), thereby completing the nep calculation, whereafter the first accumulation means 61 waits until a next input is received (step #16). Incidentally, it is desirable that the data just before it becomes higher than the threshold value is judged whether it is lower than the average value, and the value is not accumulated when it is lower than the average value.

Figure 4:
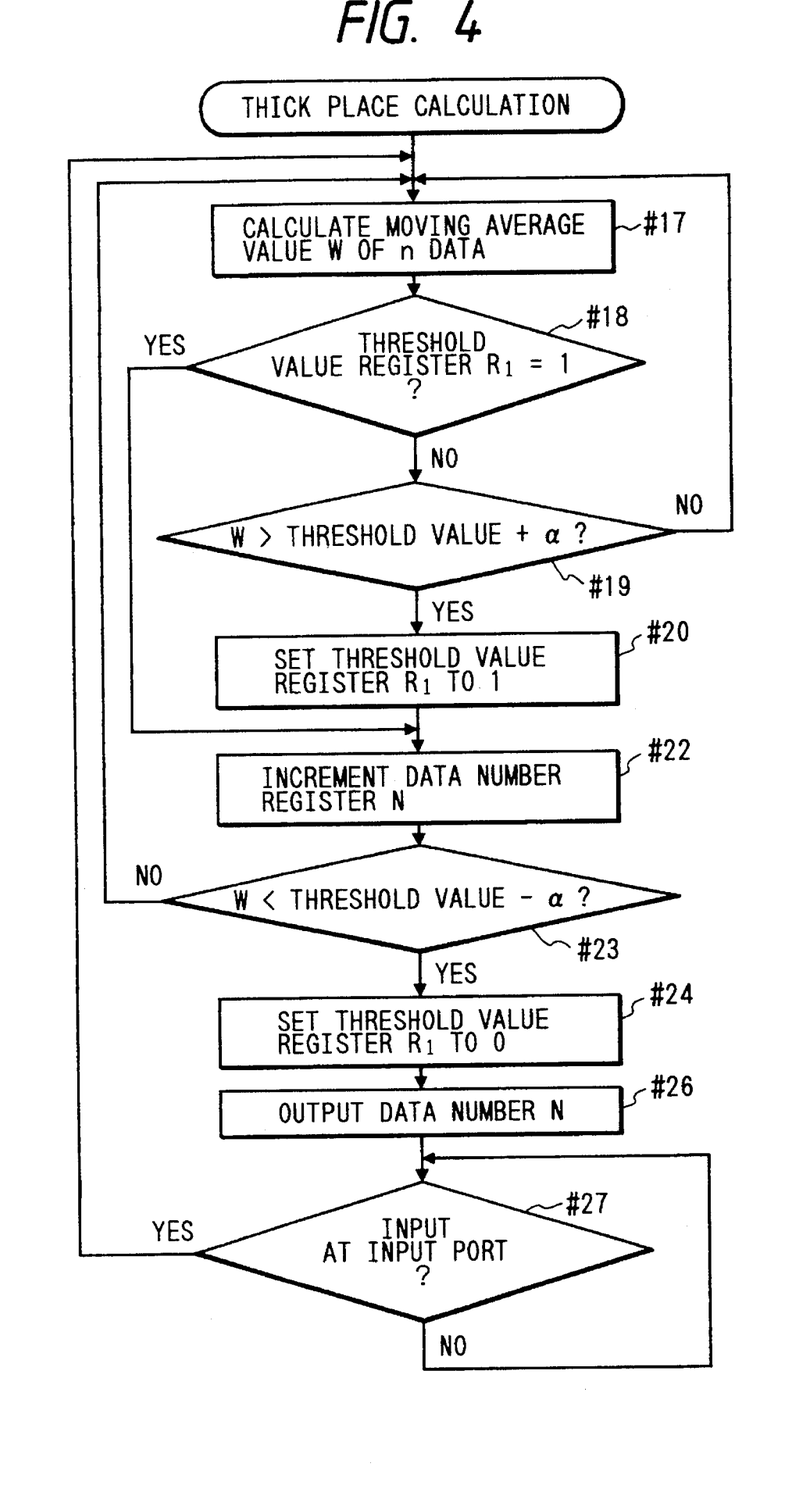
FIG. 4 is a flow chart of a thick place calculation.

FIG. 4 is a flow chart for a thick place calculation incorporated in the second accumulation means 62. Referring to FIG. 4, when an input is received (step #27), a moving average value W of last n data including the inputted data is calculated (step #17), and since the threshold value register $R_1$ is set to 0 in advance, the moving average value W is compared with an upper limit value (threshold value $+\alpha$) higher than the threshold value (, which is determined to be larger than the average value of a yarn thickness) to determine whether or not the moving average value W is higher than the upper limit value (steps #18 and #19). When the moving average value W exceeds the upper limit value, the threshold value register $R_1$ is set to 1 (step #20) and the data number register N is incremented by one (step #22). Subsequently, the moving average value W is compared with a lower limit value (threshold value $-\alpha$) lower than the threshold value to determine whether or not the moving average value W is lower than the lower limit value (step #23), and when the moving average value W is higher than the lower limit value, the control sequence returns to step #17, at which a next moving average value W is calculated. Then, since the threshold value register $R_1$ has been set to 1, the control sequence advances to step #22, at which the data number register N is incremented by one, and then the moving average value W is compared with the lower limit value to determine whether or not the moving average value W is lower than the lower limit value (step #23). Thereafter, the steps described above are repeated until after the moving average value W becomes lower than the lower limit value. Then, when the moving average value W becomes lower than the lower limit value, the threshold value register $R_1$ is reset (step #24) and the data number N is outputted (step #26), thereby completing the thick place calculation, whereafter the second accumulation means 62 waits until a next input is received (step #27).

Figure 5:
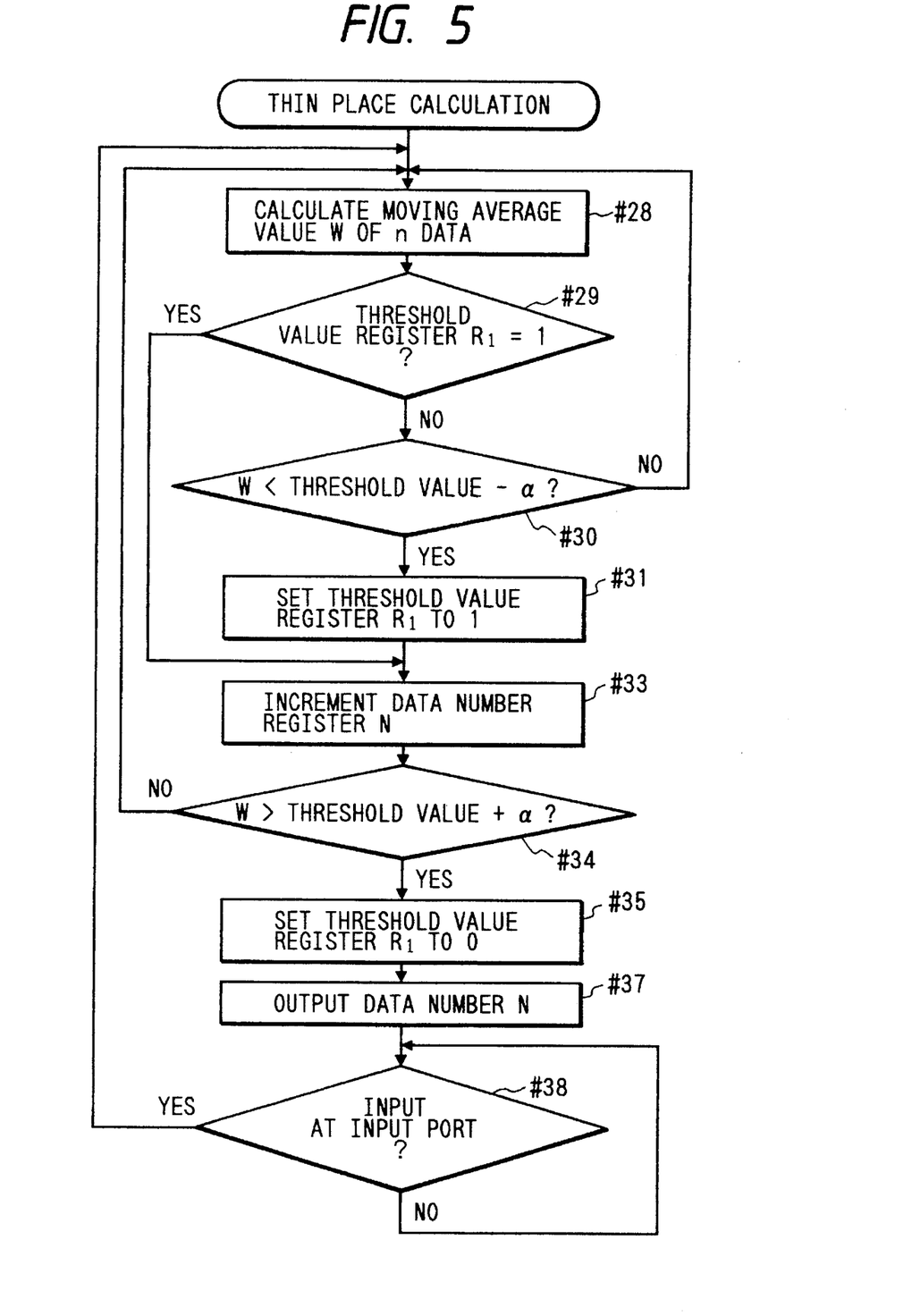
FIG. 5 is a flow chart of a thin place calculation.

FIG. 5 is a flow chart for a thin place calculation incorporated in the third accumulation means 63. Referring to FIG. 5, when an input is received (step #38), a moving average value W of last n data including the inputted data is calculated (step #28), and since the threshold value register $R_1$ is set to 0 in advance, the moving average value W is compared with a lower limit value (threshold value $-\alpha$) lower than the threshold value (, which is determined to be smaller than the average value of a yarn thickness) to determine whether or not the moving average value W is lower than the lower limit value (steps #29 and #30). When the moving average value W is lower than the lower limit value, the threshold value register $R_1$ is set to 1 (step #31) and the data number register N is incremented by one (step #33). Subsequently, the moving average value W is compared with an upper limit value (threshold value $+\alpha$) higher than the threshold value to determine whether or not the moving average value W is higher than the lower limit value (step #34), and when the moving average value W is lower than the upper limit value, the control sequence returns to step #28, at which a next moving average value W is calculated. Then, since the threshold value register $R_1$ has been set to 1, the control sequence advances to step #33, at which the data number register N is incremented by one, and then the moving average value W is compared with the upper limit value to determine whether or not the moving average value W is higher than the upper limit value (step #34). Thereafter, the steps described above are repeated until after the moving average value W becomes higher than the upper limit value. Then, when the moving average value W becomes higher than the upper limit value, the threshold value register $R_1$ is reset (step #35) and the data number N is outputted (step #37), thereby completing the thin place calculation, whereafter the third accumulation means 63 waits until a next input is received (step #38).

Figure 11:
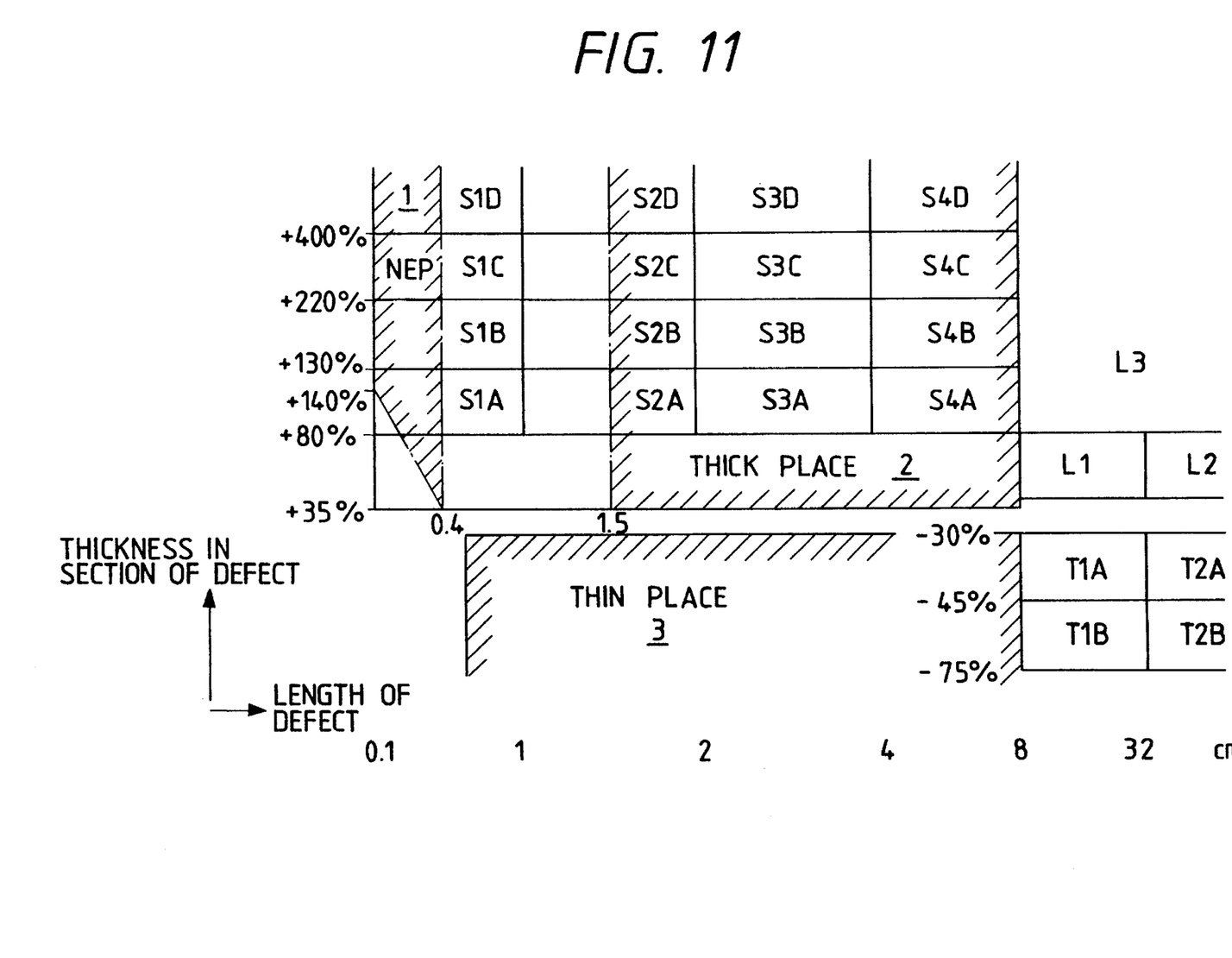
FIG. 11 is a view illustrating classification of yarn defects.

Subsequently, while operation of the second CPU of the yarn unevenness information analyzing apparatus described above, that is, an analysis of non-periodic yarn unevennesses, is described with reference to FIGS. 6 to 8, yarn defects will be described first prior to such description. Non-periodic yarn unevennesses include yarn defects which occur frequently and yarn defects which occur but seldom, and the three kinds of yarn defects of a nep, a thick place and a thin place mentioned hereinabove belong to the former, and yarn defects S1A to S4D, L1 to L3, T1A to T2B in FIG. 11 belong to the latter. Subsequently, the definitions of the three kinds of yarn defects will be described. Referring to FIG. 8, a nep 1 is a yarn defect having a defect length of 4 mm or less and a thickness larger at the defective portion thereof than +140% (1 mm conversion value); a thick place 2 is a yarn defect having a defect length of 8 cm or less and a thickness larger at the defective portion thereof than +35%; and a thin place 3 is a yarn defect having a defect length of 8 cm or less and a thickness smaller at the defective portion thereof than −30%. Meanwhile, as shown in FIG. 11, the three kinds of defects of the nep 1, the thick place 2 and the thin place 3 are relatively small comparing with the other defects A to I.

As used in the specification, the phrases long period, short period, and changeover period, are intended to respectively refer to a long time period, a short time period, and a changeover time period.

Figure 6:
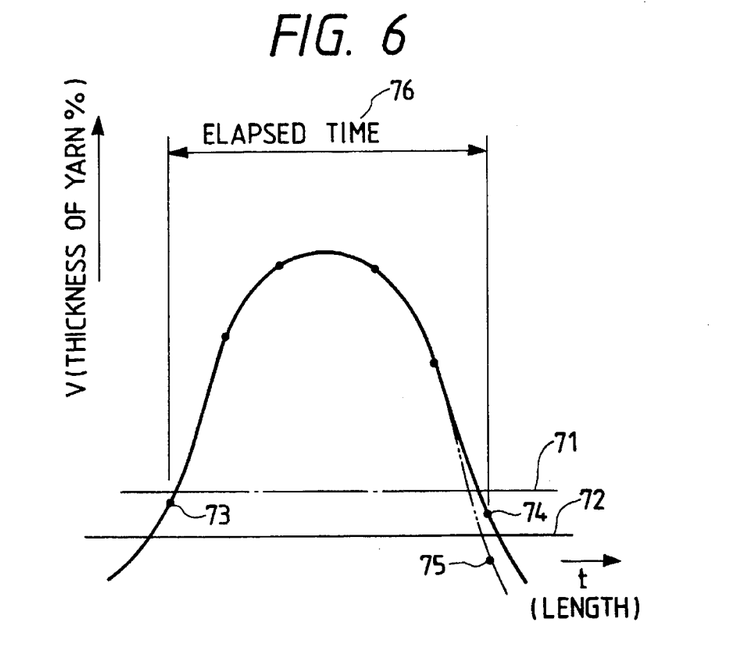
FIG. 6 is a view showing a signal waveform of a nep.

FIG. 6 shows a signal waveform of a nep. Referring to FIG. 6, the axis of ordinate represents a signal voltage V and indicates a thickness of a yarn, and the axis of abscissa represents time t and indicates a length of the yarn. The opposite ends of the signal voltage exhibit moderate gradients due to the presence of a predetermined length $\alpha$ in FIG. 10. The sampling interval is selected so that it may correspond to 1 mm when converted into the length of a yarn. That is, a yarn speed is measured and the sampling interval is varied with the yarn speed. When such a signal as illustrated in FIG. 6 is inputted, data from data 73 immediately before such data becomes higher than a threshold value 71 to another data 74 immediately after the data becomes lower than the threshold value 71 are accumulated, and the number of the data for the interval is counted. However, when the data immediately after such data becomes lower than the threshold value 71 is lower than an average value of a yarn thickness 72 as at 75, the data is not accumulated. The accumulated value is divided by the number of data to calculate a thickness of the defective portion converted into a value per 1 mm while a length of the defective portion is calculated from the data number, that is, the elapsed time 76, and they are compared with the preset values based on the definitions described above to determine whether the defect is a nep. Further, it is preferable that the data is not also accumulated in the case that the data just before it becomes higher than the threshold value 71 is to be lower than the average value 72.

Figure 7:
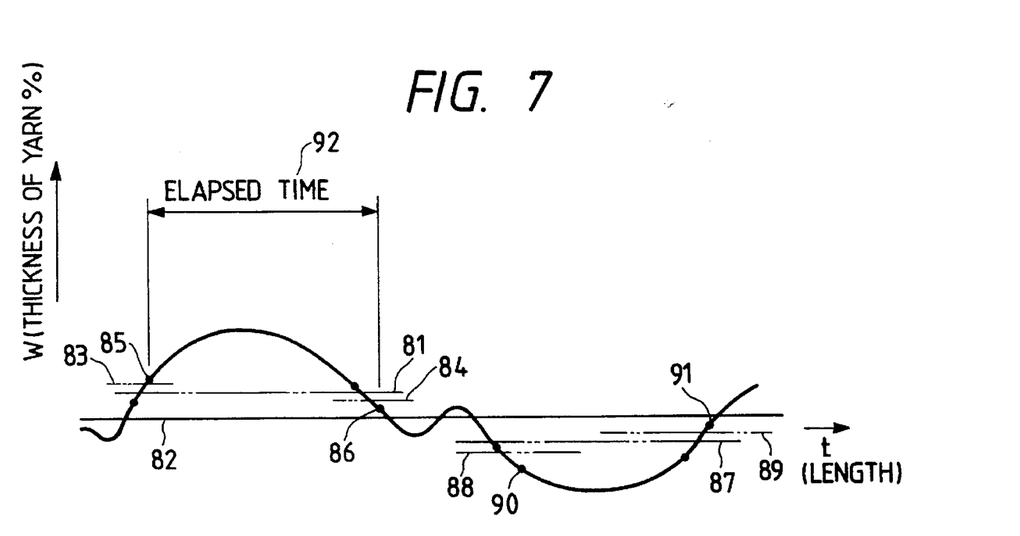
FIG. 7 is a view showing a signal waveform of a thick place.
Figure 8:
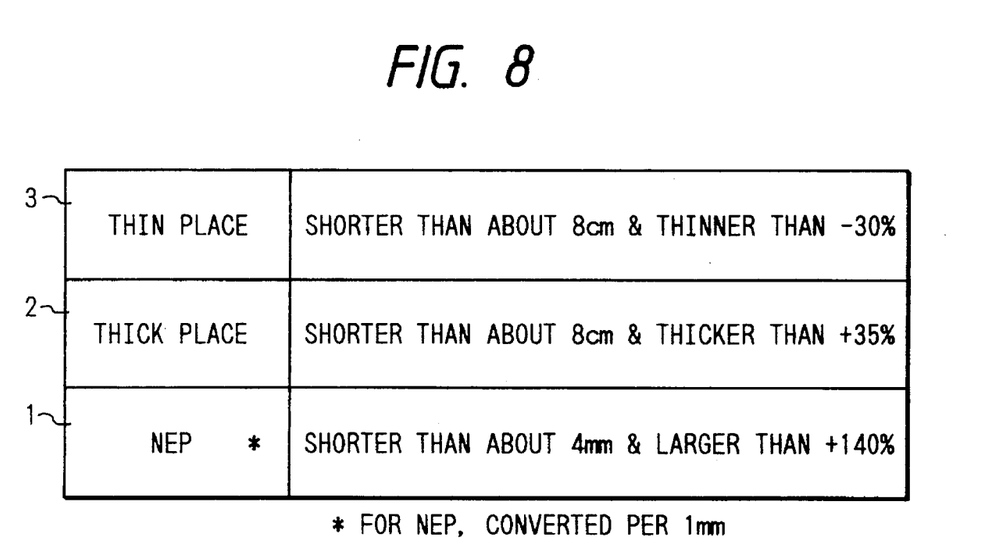
FIG. 8 is a view illustrating definitions of yarn defects.

FIG. 7 shows a waveform obtained by moving averaging of n signals of each of a thick place and a thin place. Referring to FIG. 7, the axis of ordinate represents a moving average value W of a signal voltage and indicates a thickness of a yarn, and the axis of abscissa represents time t and indicates a length of the yarn. 82 is an average value of a yarn thickness. Referring to FIG. 7, when a signal is inputted and has such a waveform as shown in FIG. 7, in the case of a thick place, the number of data is counted from a signal 85 which becomes higher than an upper limit value 83 higher than a threshold value 81 to another signal 86 which becomes lower than a lower limit value 84 lower than the threshold value 81. Meanwhile, similarly in the case of a thin place, the number of data is counted from a signal 90 which becomes lower than a lower limit value 88 lower than a threshold value 87 to another signal 91 which becomes higher than an upper limit 89 higher than the threshold value 87. In respect of an accumulated value of a yarn thickness, in the case of a thick place, the signals which are higher than a threshold value 81 are accumulated and in the case of a thin place, the signals which are lower than a threshold value 87 are accumulated.

Thereafter, similarly as in the case of a nep described above, the accumulated value and the data number are compared with the preset values based on the definitions described above to determine whether or not the yarn defect is a thick place or a thin place. (It is to be noted that the reason why the upper limit value and the lower limit value higher and lower than the threshold value, respectively, are provided is that it is intended to obtain a stabilized result even from a small variation of a signal.)

It is to be noted that operation of the first CPU of the yarn unevenness information analyzing apparatus described above, that is, contents of an analysis of periodical yarn unevennesses, are publicly known, and description of the contents is omitted herein.

Subsequently, operation of the entire yarn unevenness information analyzing apparatus described above will be described. Referring to FIG. 1, an analysis of periodical yarn unevennesses is performed such that the first multiplexer 41 is successively changed over by the changeover timing setting circuit 45 to extract yarn unevenness detection signals from the spinning units and the yarn unevenness detection signals are analyzed by the first CPU 43. The time required for the analysis is as short as 1 minute or so. Meanwhile, an analysis of non-periodic yarn unevennesses is performed similarly such that the second multiplexer 42 is successively changed over similarly to extract yarn unevenness detection signals from the spinning units and the low-pass filters 51 to 53 are changed over in accordance with a difference between long periodical unevennesses and non-periodical unevennesses or a difference in yarn speed by the third multiplexer 54 so that they may be analyzed by the second CPU 44. The time required for the analysis is as long as 4 to 10 minutes or so. By using the multiplexers and the CPU separately for an analysis of periodic yarn unevennesses and another analysis of non-periodic yarn unevennesses in this manner, the analysis of periodic unevennesses which must necessarily be performed rapidly can be performed without being restricted by the analysis of non-periodic yarn unevennesses as in the prior art.

Since a yarn unevenness information analyzing apparatus according to the present invention is constructed such that signals from a large number of yarn unevenness detectors are inputted to calculation means for yarn unevenness analysis by way of first changeover means for changing over the signals in a short period to successively output the signals and second changeover means for changing over the signals in a long period to successively output the signals as described above, an analysis of yarn unevennesses of a short period can be performed without being restricted by another analysis of yarn unevennesses of a long period. Consequently, it is possible to perform rapid maintenance of rollers and so forth of the spinning machine.

Figure 12:
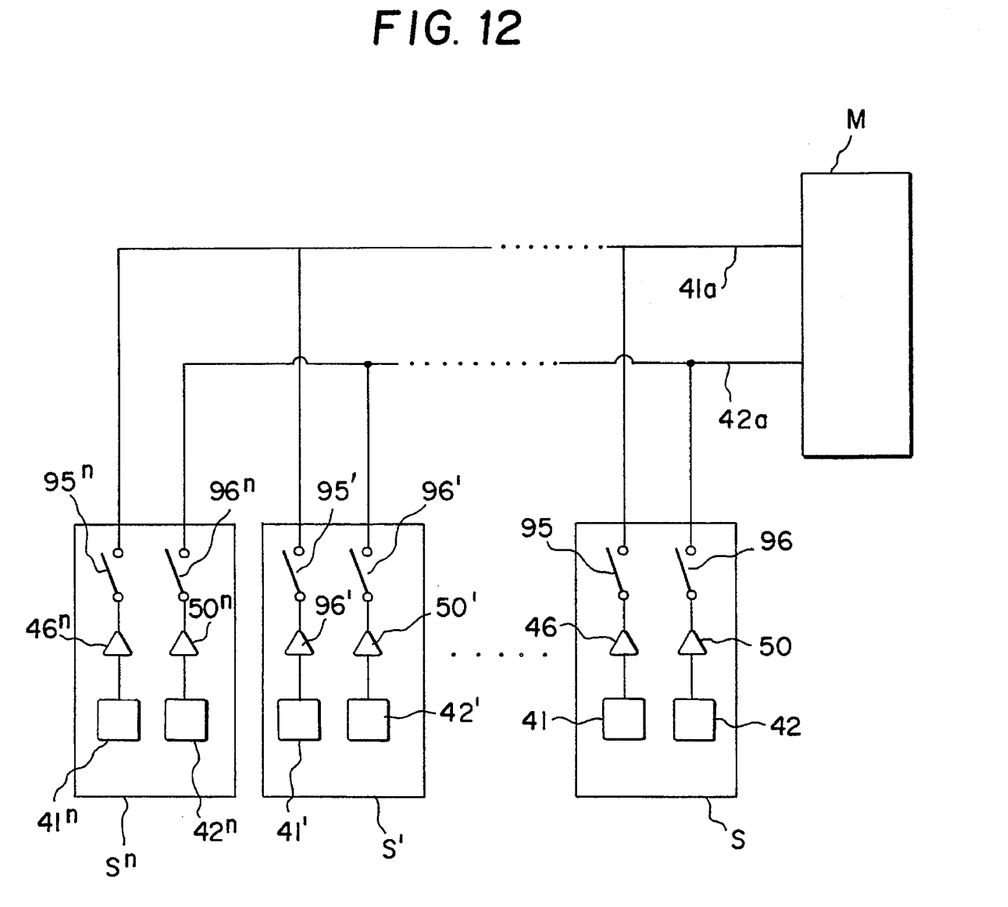
FIG. 12 illustrates yarn unevenness detectors arranged in groups.

In the above description, only two changeover means are provided. However, more than three changeover means may be provided. FIG. 12 illustrates groups S, S', ..., $S^n$, of yarn unevenness detectors, which are connected to the master M via the analog lines 41a and 42a in a manner similar to that shown in FIG. 1. The elements 95—$95^n$ and 96—$96^n$ in each of the groups S, S', ..., $S^n$, respectively constitute another changeover means for selecting one of the groups S, S', ..., $S^n$. The right half of FIG. 12 is shown in detail in FIG. 1.

Furthermore, according to a yarn defect detection method of the present invention, since, based on an electric signal, for a thin and long defect, accumulation is started from a signal which becomes lower than a lower limit value lower than a predetermined threshold value and is performed to another signal which becomes higher than an upper limit value higher than the predetermined threshold value, whereas, for a thick and long defect, accumulation is started from a signal which becomes higher than an upper limit value higher than a predetermined threshold value and is performed to another signal which becomes lower than a lower limit lower than the predetermined threshold value, those defects can be detected accurately from a fine variation of the value around the threshold value. Accordingly, it is possible to evaluate a fine quality on the on-line real-time basis, and only by additionally installing detectors, the present yarn defect detection method can be applied to a large number of spinning units with a single analyzing apparatus.

What is claimed is:

1. A yarn unevenness information analyzing apparatus which receives signals from a plurality of yarn unevenness detectors, the apparatus comprising:

calculation means receiving the signals from the plurality of yarn unevenness ydetectors, for analyzing yarn unevenness, said calculation means including a central processing unit portion; and a first changeover means receiving the signals from said plurality of yarn unevenness detectors for sequentially connecting signals from each of said plurality of yarn unevenness detectors in a first predetermined time period to successively output the signals to said calculation means, and a second changeover means independently receiving the signals from said plurality of yarn unevenness detectors for sequentially connecting signals from each of said plurality of yarn unevenness detectors in a second predetermined time period which is different from said first predetermined time period to successively output the signals to said calculation means, wherein said first changeover means and said second changeover means are operated independently from each other so that both of a periodical yarn unevenness in said first predetermined time period and a yarn unevenness in said second predetermined time period can be simultaneously analyzed.

2. A yarn unevenness information analyzing apparatus as claimed in claim 1, wherein the signals from said plurality of yarn unevenness detectors are inputted to said calculation means by said first changeover means for successively outputting the signals to said calculation means for said first predetermined time period, and the signals from said plurality of yarn unevenness detectors are input to said calculation means by said second changeover means for successively outputting the signals to said calculation means for said second predetermined time period which is substantially longer than said first predetermined time period.

3. A yarn unevenness information analyzing apparatus as claimed in claim 2, wherein said calculation means for analyzing yarn unevenness comprises a first analyzing means for analyzing yarn unevenness over said first predetermined time period and a second analyzing means for analyzing yarn unevenness over said second predetermined time period which is substantially longer than said first predetermined time period.

4. A yarn unevenness information analyzing apparatus as claimed in claim 1, further comprising a sampling means for sampling an input signal provided from said changeover means to said calculating means, said sampling means being disposed at an intermediate location between said changeover means and said calculation means.

5. A yarn unevenness information analyzing apparatus as claimed in claim 1, further comprising a communication line for performing signal transmission between said calculation means and said plurality of changeover means.

6. A yarn unevenness information analyzing apparatus as claimed in claim 1, further comprising a changeover timing setting means for setting said changeover time period for each changeover means, said changeover timing setting means being disposed in a signal path between said calculation means and said plurality of changeover means.

* * * * *